US011517514B2

(12) United States Patent
Consoli et al.

(10) Patent No.: US 11,517,514 B2
(45) Date of Patent: Dec. 6, 2022

(54) RESORCINOL-FREE HAIR COLOURING COMPOSITIONS

(71) Applicant: BEAUTY & BUSINESS S.p.A., Milan (IT)

(72) Inventors: Antonio Consoli, Urgnano (IT); Katiuscia Grevalcuore, Bergamo (IT); Monica Besozzi, Pontirolo Nuovo (IT); Emanuela Facchetti, Romano di Lombardia (IT); Massimo Fabbi, Mozzo (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 0 days.

(21) Appl. No.: 17/655,585

(22) Filed: Mar. 21, 2022

(65) Prior Publication Data

US 2022/0304908 A1 Sep. 29, 2022

(30) Foreign Application Priority Data

Mar. 25, 2021 (IT) .................... 102021000007352

(51) Int. Cl.
*A61Q 5/10* (2006.01)
*A61K 8/41* (2006.01)
*A61K 8/49* (2006.01)

(52) U.S. Cl.
CPC .............. *A61K 8/415* (2013.01); *A61K 8/494* (2013.01); *A61K 8/4926* (2013.01); *A61K 8/4973* (2013.01); *A61Q 5/10* (2013.01); *A61K 2800/30* (2013.01); *A61K 2800/4324* (2013.01); *A61K 2800/591* (2013.01); *A61K 2800/882* (2013.01)

(58) Field of Classification Search
CPC .. A61Q 5/10; A61K 8/415; A61K 2800/4324; A61K 2800/882; A61K 8/4926; A61K 8/4973; A61K 2800/30
USPC .......................................................... 8/405
See application file for complete search history.

(56) References Cited

U.S. PATENT DOCUMENTS

| 8,523,956 | B2 * | 9/2013 | Wood ................. A61Q 5/10 8/408 |
| 8,608,810 | B2 * | 12/2013 | Sutton ................ A61K 8/415 8/408 |
| 8,663,340 | B2 * | 3/2014 | Sutton ................ A61Q 5/10 8/405 |
| 8,709,102 | B2 * | 4/2014 | Wood ................. C09B 1/207 8/405 |
| 2007/0186357 | A1 | 8/2007 | Chalmers et al. |
| 2013/0269121 | A1 * | 10/2013 | Pratt .................. A61Q 5/10 8/405 |
| 2016/0208103 | A1 * | 7/2016 | Bachmann ........... C07D 213/56 |
| 2017/0216174 | A1 * | 8/2017 | Aeby .................. A61Q 5/08 |

FOREIGN PATENT DOCUMENTS

| EP | 1166748 | * | 1/2002 | .............. A61Q 5/10 |
| EP | 1166748 | A2 | 1/2002 | |
| FR | 2831057 | * | 4/2003 | .............. A61Q 5/10 |
| FR | 2831057 | A1 | 4/2003 | |

OTHER PUBLICATIONS

Search Report of priority application No. IT202100007352 dated Dec. 24, 2021.

* cited by examiner

*Primary Examiner* — Eisa B Elhilo
(74) *Attorney, Agent, or Firm* — Silvia Salvadori, P.C.; Silvia Salvadori

(57) ABSTRACT

The present invention relates to hair colouring compositions free of resorcinol, 2-methyl resorcinol, 4-chloro resorcinol and resorcinol derivatives and free of methoxymethyl-p-phenylenediamine, said compositions comprising at least three dyes selected from at least one primary dye selected from p-toluenediamine sulphate, p-aminophenol, N-methyl-p-aminophenol sulphate and 1-hydroxyethyl-4,5-diamino pyrazole sulphate, and at least two secondary dyes selected from hydroxyethyl 3,4-methylenedioxyaniline HCl, 2-amino-3-hydroxypyridine and 2-methyl-5-hydroxyethyl-aminophenol, or at least two primary dyes selected from p-toluenediamine sulphate, p-aminophenol, N-methyl-p-aminophenol sulphate and 1-hydroxyethyl-4,5-diamino pyrazole sulphate, and at least one secondary dye selected from hydroxyethyl 3,4-methylenedioxyaniline HCl, 2-amino-3-hydroxypyridine and 2-methyl-5-hydroxyethyl-aminophenol.

7 Claims, No Drawings

RESORCINOL-FREE HAIR COLOURING COMPOSITIONS

This Application claims priority to and the benefit of Italian Patent Application no. 102021000007352 filed on Mar. 25, 2021, the content of which is incorporated herein by reference in its entirety.

The present invention relates to hair colouring compositions comprising a mixture of oxidative dyes and not containing resorcinol.

PRIOR ART

Hair colouring is one of the main cosmetic hair treatments. The main hair-dyeing methods are the semi-permanent system and the permanent oxidative system. The first involves the use of direct dyes which are deposited on the hair surface. With this system, the colour gradually fades every time the hair is shampooed, and eventually disappears within 10 washes.

In the permanent system, colour is created by the reaction of primary intermediates and couplers in the presence of an oxidant. The stability of the dye to washing ranges between four and eight weeks in this case. The oxidative system is based on the reaction of "primary intermediates" with couplers, both of which are practically colourless. In the presence of air or oxidants such as hydrogen peroxide, primary dyes, which are typically primary aromatic amines with a hydroxyl or additional amino group, substituted or not substituted in the para or ortho position, react with couplers (secondary dyes) such as resorcinol, m-aminophenol, m-phenylenediamine and 1-naphthol.

As the dye molecules thus formed in the cuticle are larger than the starting primary intermediates and the highly diffusible couplers, they remain trapped inside the hair, and there is therefore no significant fading due to successive washes or the action of external agents.

The primary dye which was historically most widely used to produce oxidative dyes was p-phenylenediamine (PPD), later replaced by p-toluenediamine (PTD), which is less inclined to cause sensitisation problems such as contact dermatitis or more serious allergic reactions, including anaphylactic shock. p-amino-phenol (PAP) is generally used as primary dye together with PPD/PTD.

Resorcinol is one of the fundamental couplers (secondary dye) in hair colouring preparations containing PPD, PTD and PAP because when combined with them, it gives the color component required to create natural nuances. In particular, PAP+resorcinol provides a yellow/green component essential to create brown and blonde shades.

In February 2020, at the request of the European Commission, some member states of the ECHA (European Chemicals Agency) opened a file on the identification of 5 substances as SVHCs (Substances of Very High Concern). The file was prepared in accordance with the requirements of ANNEX XV to REACH, and includes resorcinol as an endocrine disrupter.

Although the public consultation is still ongoing, many cosmetic companies in the hair colouring field have already taken steps to eliminate resorcinol from their products on the market, replacing it with 2-methyl resorcinol and/or 4-chloro resorcinol.

4-chloro resorcinol is used to give a cool/yellow-green tone in combination with p-aminophenol (PAP), a tone similar to that provided by the resorcinol+PAP combination. 2-methyl resorcinol provides a warm/yellow-gold tone in combination with PAP. Said two yellow tones are essential for the creation of natural shades.

It is therefore evident that removal of all resorcinols from the formula constitutes a major technical problem in the creation of natural colours ranging from dark brown to light blonde.

2-Methyl-resorcinol is known to affect the human endocrine system (Toxicological Sciences, 156 (1), 2017, 240-251).

4-chloro-resorcinol has a structure similar to those of resorcinol and 2-methyl resorcinol, and also contains up to 1% of resorcinol impurities (see opinion SCCS/1224/09); it therefore plausibly has a biological activity similar to that of resorcinol.

There is consequently a need to create a permanent oxidative dye that does not contain resorcinol or derivatives thereof such as 2-methyl resorcinol and 4-chloro-resorcinol, and is therefore safer for the user's health in terms of endocrine disruption, but without limiting the range of shades available to users, especially as regards the availability of natural shades ranging from brown to blonde.

Definitions

The International Colour Chart (ICC) is a system used to classify hair colouring preparations. This means that every hair colouring preparation (shade or nuance) has a code defining its colour result. Said code can be used by manufacturers of colour charts or hair colouring preparations. In practice, the ICC system uses numbers to define the depth (level) and tone of a given colour.

The colour "level" indicates how light or dark the shade is. The ICC (International Colour Chart) system uses numbers to define the depth of colour. Said values range from 1 to 11, wherein 1 denotes the darkest shade (black) and 11 the lightest shade (platinum blonde).

The usual level numbers and names are as shown in Table A.

TABLE A

| Level | Level name |
|---|---|
| 1 | Black |
| 2 | Very dark brown |
| 3 | Dark brown |
| 4 | Medium brown |
| 5 | Light brown |
| 6 | Dark blonde |
| 7 | Medium blonde |
| 8 | Light blonde |
| 9 | Very light blonde |
| 10 | Lightest blonde |
| 11 | Platinum blonde |

The tone indicates how cool or warm a colour is, and includes colours such as gold, ash and copper.

Although the level measurement is almost identical for all manufacturers, each manufacturer follows its own system when classifying tone. Tone is indicated by a number, usually placed after the level, separated by a decimal point ".", a comma "," or a slash "/". The classification followed by the Applicant is set out below:

| Tone number | Tone name |
|---|---|
| 0 | Natural (grey-neutral) |
| 1 | Ash (blue) |

-continued

| Tone number | Tone name |
|---|---|
| 2 | Irisé (violet) |
| 3 | Gold (yellow) |
| 4 | Copper (orange) |
| 5 | Mahogany (violet red) |
| 6 | Red (red) |
| 7 | Matte (green) |
| 8 | Pearl |

Some hair colouring preparations can have a double tone, and it is usual to place two numbers after the decimal point of the level to express said characteristic. For example, if the colour chart contains the number 7.21, the first number indicates the medium blonde level (7), the second indicates the irisé tone (2), and the third number indicates a second ash tone (3). Said colour will be called "medium blonde irisé ash".

DESCRIPTION OF THE INVENTION

The invention relates to compositions free of resorcinol and derivatives thereof such as 2-methyl-resorcinol and 4-chloro resorcinol, said compositions comprising at least three dyes selected from: at least one primary dye selected from p-toluenediamine sulphate (PTD); p-aminophenol (PAP); N-methyl-p-aminophenol sulphate (photo rex); 1-hydroxyethyl-4,5-diamino pyrazole sulphate and at least two secondary dyes selected from hydroxyethyl 3,4-methylenedioxyaniline HCl (HMOC); 2-amino-3-hydroxypyridine; 2-methyl-5-hydroxyethylaminophenol, or at least two primary dyes selected from p-toluenediamine sulphate, p-aminophenol, N-methyl-p-aminophenol sulphate and 1-hydroxyethyl-4,5-diamino pyrazole sulphate, and at least one secondary dye selected from hydroxyethyl 3,4-methylenedioxyaniline HCl, 2-amino-3-hydroxypyridine and 2-methyl-5-hydroxyethylaminophenol.

The compositions can also contain additional oxidative dyes. The compositions according to the invention do not contain methoxymethyl-p-phenylenediamine (MBB).

Wella EP1166748 discloses the combination of at least one 4,5-diaminopyrazole derivative with at least one ingredient selected from 5-amino-2-methylphenol derivatives and m-phenylenediamine derivatives. However, in the text, neither 2-amino-3-hydroxypyridine nor 2-methyl-5-hydroxyethylaminophenol is specified among the additional dyes. It is stated on page 3 that in order to modulate the colour result and produce special colour effects, said combination of dyes can be supplemented with other conventional oxidative dyes, including resorcinol derivatives. This demonstrates that the use of resorcinol and derivatives thereof is required by the skilled person to obtain a wide range of colours.

Oreal FR2831057 discloses the combination of at least one p-phenylenediamine dye with a p-aminophenol dye plus an m-aminophenol derivative and 1-N-(3-hydroxyethyl) 4-hydroxyindole. It is stated on page 9 that the composition can contain one or more conventional couplers commonly used for colouring keratin fibres; m-diphenols are cited as an example. On pages 1 and 2 it is clearly explained that a variety of dye couplers is useful to obtain a wide palette of colours, demonstrating that the elimination of resorcinol and derivatives thereof constitutes a challenging task for hair dye formulators.

The technical problem of creating all possible shades, especially natural shades, without using resorcinol or derivatives thereof, has therefore been solved by using specific ternary combinations of dyes.

The production of ternary combinations of dyes to obtain all the tones required to create an entire colour chart is challenging, and requires in-depth studies of the reaction kinetics of the dyes concerned. The use of the dye combinations according to the invention allows the formulation of any colour without using resorcinols, and surprisingly reduces the total amount of dyes used. The formulas contain 10-50% less dyes than formulas with resorcinols. On average, there is a 25% reduction in the total dyes used in each shade. The maximum percentage of total oxidative dyes is 6% by weight respect to the weight of the composition.

In particular, there is a reduction in the percentage of PTD sulphate, a dye indicated as an extreme sensitiser with an EC3 of 0.31% in opinion 1509/13 of the Scientific Committee on Consumer Safety (SCCS), "Memorandum on hair dye chemical sensitization", dated 26 Feb. 2013.

The percentage of PTD present in each formula is not more than 3% by weight, preferably less than 2%.

The total reduction in the percentage of dyes used, in particular of PTD sulphate, involves two advantages:
1) greater stability of the formulas, because large amounts of salified dyes are known to cause separation of emulsions
2) safer formulas, because dyes are among the ingredients that pose the greatest health risk to users.

The compositions according to the invention, mixed at a suitable dilution with an activator, dye the hair permanently and stably, without unwanted colour changes.

"Activator" means hydrogen peroxide, carbamide peroxide, perborates and persulphates or peracids. The preferred compound is hydrogen peroxide. The amount can range from 0.1 to 50%.

The compositions according to the invention can optionally be in "ready-to-use" form, comprising two or more ingredients to be mixed before use. Depending on their composition, the ready-to-use hair colouring preparations according to the invention can be weakly acidic, neutral or alkaline, and have a pH ranging from about 3 to 11, preferably from 6.5 to 11.

The composition comprises an alkalising agent selected, for example, from ammonia, monoethanolamine (MEA), 1-amino-2-propanol, 2-amino-2-methyl-propanol (AMP), 2-amino-2-methyl-1,3-propanediol, 2-amino-2-ethyl-1,3-propanediol and tris(hydroxymethyl)-aminomethane (tromethamine, Tris), sodium hydroxide, potassium hydroxide, urea, allantoin, arginine, lysine, tripotassium phosphate, sodium saccharine, triethanolamine (TEA) or combinations thereof.

The amount of alkalising agent can range between 0.1 and 20% by weight, preferably between 0.2 and 10% by weight.

The composition according to the invention can also contain other oxidative dyes in addition to those of combinations a) and b) cited above.

The preferred dyes are listed below according to the INCI nomenclature (International Nomenclature of Cosmetic Ingredients):
p-phenylenediamine (PPD); p-toluenediamine sulphate (PTD); 2,4,5,6-tetraaminopyrimidine (TAP); hydroxyethyl-p-phenylenediamine sulphate; N,N-di-(2-hydroxyethyl)-p-phenylenediamine sulphate (BETOXOL); p-aminophenol (PAP); 4-amino-3-methyl-phenol; 1-hydroxyethyl-4,5-diamino pyrazole sulphate, 1-Acetoxy-2-Methylnaphthalene, 5-Amino-4-Chloro-o-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-

Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulphate, 2-Amino-4-Hydroxyethylaminoanisole, 2-Amino-4-Hydroxyethylaminoanisole, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, 4-Chloro-2-Aminophenol, 2-Chloro-p-Phenylenediamine, N-Cyclopentyl-m-Aminophenol, 3,4-Diaminobenzoic Acid, 4,5-Diamino-1-((4-Chlorophenyl)Methyl)-1H-Pyrazole-Sulphate, 2,3-Diaminodihydropyrazolo Pyrazolone Dimethosulphonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-Fluoro-6-Methyl-m-Phenylenediamine, 1-Hexyl 4,5-Diamino Pyrazole Sulphate, Hydroquinone, Hydroxyanthraquinoneaminopropyl Methyl Morpholinium Methosulphate, Hydroxybenzomorpholine, Hydroxyethoxy Aminopyrazolopyridine, Hydroxyethylaminomethyl-p-Aminophenol, Hydroxyethyl-2,6-Dinitro-p-Anisidine, 2-Hydroxyethyl Picramic Acid, 6-Hydroxyindole, Hydroxypropyl Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethylaminophenol, Methylimidazoliumpropyl p-Phenylenediamine, 2-Methyl-1-Naphthol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, Phenyl Methyl Pyrazolone, N-Phenyl-p-Phenylenediamine, Picramic Acid, Pyrocatechol, Pyrogallol, Sodium Picramate, Tetrahydro-6-Nitroquinoxaline, Toluene-2,6-Diamine, Toluene-3,4-Diamine, 2,5,6-Triamino-4-Pyrimidinol, 1,2,4-Trihydroxybenzene.

The oxidative dyes can be in the form of salts. The hair colouring preparations according to the invention can also contain direct dyes. Examples of direct dyes, defined according to the INCI nomenclature (European Community Decision 2006/257/EC as amended—International Nomenclature of Cosmetic Ingredients), include:

Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 377, Disperse Brown 1, Disperse Orange 3, Disperse Red 11, Disperse Red 15, Disperse Red 17, Disperse Violet 1, Disperse Violet 4, Disperse Violet 15, HC Blue No. 2, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Brown No. 1, HC Brown No. 2, HC Green No. 1, HC Orange No. 1, HC Orange No. 2, HC Orange No. 3, HC Orange No. 5, HC Orange No. 6, HC Red No. 1, HC Red No. 3, HC Red No. 7, HC Red No. 8, HC Red No. 9, HC Red No. 10, HC Red No. 11, HC Red No. 13, HC Red No. 14, HC Red No. 15, HC Red No. 17, HC Red No. 18, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, HC Yellow No. 16, HC Yellow No. 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline.

The hair colouring preparations according to the invention can also contain one or more natural or synthetic additives commonly used in the cosmetics industry, such as solvents, surfactants, emulsifiers, wetting agents, thickeners, conditioners, etc.

Examples of solvents include water, low-molecular-weight aliphatic mono- or polyalcohols, esters and ethers thereof, for example alkanols, in particular having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, dipropylene glycol, polyalkylene glycols, such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxyethyl ester; amides such as N-methylpyrrolidone; urea, tetramethyl urea and thiodiglycol.

The following can also be present: anionic, cationic, non-ionic, amphoteric or zwitterionic emulsifiers; wetting agents; surfactants, such as fatty alcohol sulphates, alkylsulphonates, alkylbenzene sulphonates, alklymethyl ammonium salts, alkylbetaine, α-olefin sulphonates, ethoxylated fatty alcohols, fatty acid alkanolamines, ethoxylated esters of fatty acids, polyglycol ether sulphates of fatty acids and alkylpolyglycosides, thickeners, such as higher fatty alcohols, starches, cellulose derivatives, vaseline, paraffin oil, fatty acids and other fatty ingredients in emulsified form, water-soluble polymer thickeners, such as natural gums, guar gum, tara gum, xanthan gum, carob flour, pectin, dextran, agar-agar, amylose, amylopectin, dextrin, synthetic clays or hydrocolloids, such as polyvinyl alcohol; conditioning and restructuring agents such as lanolin derivatives, cholesterol, pantothenic acid, water-soluble cationic polymers, protein derivatives, amino acids, provitamins, vitamins, plant extracts, sugar and betaine; auxiliary agents such as electrolytes, antioxidants, fatty amides, sequestering agents, film-forming agents and preservatives, and beeswax.

The addition to the hair colouring preparations according to the invention of non-ionic and/or anionic surfactants, such as fatty alcohol sulphates, in particular lauryl sulphate or sodium cocoyl sulphate; ethoxylated fatty alcohol sulphates, in particular sodium lauryl ether sulphates with 2 to 4 molecular units of ethylene oxide, ethoxylated esters of fatty acids, ethoxylated nonylphenols, ethoxylated fatty alcohols, alkylbenzene sulphonates or alkanolamides of fatty acids, in a total amount preferably ranging from about 0.1 to 30% by weight, more preferably from 0.2 to 15% by weight, can be particularly advantageous.

Examples of useful cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Other useful cationic surfactants are quaternised protein hydrolysates.

As well as non-ionic organic thickeners with properties similar to wax and non-ionic surfactants, the hair colouring preparation can include the usual cosmetic cationic resins. Polyquaternium-6, Polyquaternium-7, Polyquaternium-10, Polyquaternium-11, Polyquaternium-22, Polyquaternium-35, Polyquaternium-37 and Polyquaternium-113, either alone or mixtures thereof, are particularly preferred.

Examples

The ingredients listed in the examples are named according to the INCI nomenclature (European Community Decision 2006/257/EC as amended—International Nomenclature of Cosmetic Ingredients).

Table 1 shows the formulas of the activators used. Formulas A1, A2, A3 and A4 represent the different strengths of the activators, namely 40, 30, 20 and 10 volumes respectively.

TABLE 1

| | Activators | | | |
|---|---|---|---|---|
| INGREDIENTS | A1 % | A2 % | A3 % | A4 % |
| AQUA (WATER) | q.s. to 100 | q.s. to 100 | q.s. to 100 | q.s. to 100 |
| HYDROGEN PEROXIDE | 12 | 9 | 6 | 3 |
| CETEARYL ALCOHOL | 3 | 3 | 3 | 3 |
| CETEARETH-20 | 0.6 | 0.6 | 0.6 | 0.6 |
| PHOSPHORIC ACID | 0.1 | 0.1 | 0.1 | 0.1 |
| SODIUM STANNATE | 0.2 | 0.2 | 0.2 | 0.2 |
| SODIUM LAURETH SULPHATE | 0.1 | 0.1 | 0.1 | 0.1 |
| PROPYLENE GLYCOL | 0.5 | 0.5 | 0.5 | 0.5 |
| DISODIUM PYROPHOSPHATE | 0.1 | 0.1 | 0.1 | 0.1 |
| DIMETHICONE | 0.1 | 0.1 | 0.1 | 0.1 |
| PEG-40 CASTOR OIL | 0.5 | 0.5 | 0.5 | 0.5 |
| PENTASODIUM PENTETATE | 0.1 | 0.1 | 0.1 | 0.1 |
| ETIDRONIC ACID | 0.1 | 0.1 | 0.1 | 0.1 |

Table 2 shows the compositions of the hair colouring preparations in cream form used in the tests described below.

Compositions F2*F4*F6* are those according to the invention, while compositions F1, F3 and F5 are STANDARD comparative formulas containing resorcinols.

TABLE 2

| | Compositions in cream form | | | | | |
|---|---|---|---|---|---|---|
| | F1 (shade 5.0) | F2* (shade 5.0) | F3 (shade 5.66I) | F4* (shade 5.66I) | F5 (shade 1.0) | F6* (shade 1.0) |
| AQUA (WATER) | q.s. to 100 | q.s. to 100 | q.s. to 100 | q.s. to 100 | q.s. to 100 | q.s. to 100 |
| CETEARYL ALCOHOL | 8 | 8 | 8 | 8 | 8 | 8 |
| CETEARETH-50 | 7 | 7 | 7 | 7 | 7 | 7 |
| STEARYL ALCOHOL | 6 | 6 | 6 | 6 | 6 | 6 |
| PROPYLENE GLYCOL | 5 | 5 | 5 | 5 | 5 | 5 |
| LAURYL ALCOHOL | 2.8 | 2.8 | 2.8 | 2.8 | 2.8 | 2.8 |
| PEG-40 HYDROGENATED CASTOR OIL | 2 | 2 | 2 | 2 | 2 | 2 |
| COCAMIDOPROPYL BETAINE | 1.2 | 1.2 | 1.2 | 1.2 | 1.2 | 1.2 |

TABLE 2-continued

Compositions in cream form

| | F1 (shade 5.0) | F2* (shade 5.0) | F3 (shade 5.66I) | F4* (shade 5.66I) | F5 (shade 1.0) | F6* (shade 1.0) |
|---|---|---|---|---|---|---|
| MYRISTYL ALCOHOL | 1.2 | 1.2 | 1.2 | 1.2 | 1.2 | 1.2 |
| PARFUM (FRAGRANCE) | 0.8 | 0.8 | 0.8 | 0.8 | 0.8 | 0.8 |
| DECYLTETRADECANOL | 0.7 | 0.7 | 0.7 | 0.7 | 0.7 | 0.7 |
| SODIUM SULPHITE | 0.4 | 0.4 | 0.4 | 0.4 | 0.4 | 0.4 |
| ERYTHORBIC ACID | 0.3 | 0.3 | 0.3 | 0.3 | 0.3 | 0.3 |
| POLYQUATERNIUM-22 | 0.2625 | 0.2625 | 0.2625 | 0.2625 | 0.2625 | 0.2625 |
| EDTA | 0.2 | 0.2 | 0.2 | 0.2 | 0.2 | 0.2 |
| BISABOLOL | 0.1 | 0.1 | 0.1 | 0.1 | 0.1 | 0.1 |
| OLETH-5 PHOSPHATE | 0.1 | 0.1 | 0.1 | 0.1 | 0.1 | 0.1 |
| DIOLEYL PHOSPHATE | 0.1 | 0.1 | 0.1 | 0.1 | 0.1 | 0.1 |
| TOLUENE-2,5-DIAMINE SULPHATE | 2.08 | 0.953 | — | — | 4.3 | 3 |
| 1-HYDROXYETHYL 4,5-DIAMINO PYRAZOLE SULPHATE | — | — | 2.39 | 1.785 | 0.08 | 0.05 |
| p-AMINOPHENOL | — | — | 0.34 | — | — | — |
| 2,4-DIAMINOPHENOXYETHANOL HCl | 0.07 | 0.07 | 0.468 | 0.38 | 0.56 | 0.4 |
| HYDROXYETHYL 3,4-METHYLENEDIOXYANILINE HCL | — | 0.407 | — | — | — | 1.4 |
| 2-AMINO-3-HYDROXYPYRIDINE | — | 0.12 | — | 0.1 | — | 0.15 |
| 2-METHYLRESORCINOL | 0.271 | — | — | — | 0.1 | — |
| RESORCINOL | 0.63 | — | 0.025 | — | 1 | — |
| m-AMINOPHENOL | 0.136 | 0.12 | 0.975 | 0.699 | 0.7 | 0.49 |
| p-METHYLAMINOPHENOL SULPHATE | — | — | — | 0.353 | — | — |
| 2-METHYL-5-HYDROXYETHYLAMINOPHENOL | — | — | — | 0.1 | — | — |
| ETHANOLAMINE (MEA) | 0.95 | 0.71 | 1.75 | 0.88 | 4 | 2.8 |
| AMMONIA | 1.8 | 1.8 | 1.8 | 1.8 | 1.2 | 1.2 |
| Total dyes | 3.18 | 1.67 | 4.198 | 3.417 | 6.84 | 5.49 |

It should be noted that formula F2* according to the invention contains 47% less dyes, and in particular 54% less p-toluenediamine (PTD).

Formula F4* according to the invention contains 18% less total dyes.

Formula F6* according to the invention contains 19% less dyes, and in particular 30% less p-toluenediamine (PTD).

Table 3 shows examples of hair colouring preparations in gel form.

Composition F8* is a formula according to the invention, while F7 is a STANDARD comparative formula containing resorcinols.

TABLE 3

Gel compositions shade 6.3 (dark blonde gold)

| Ingredients (INCI) | F7 | F8* |
|---|---|---|
| AQUA | q.s. to 100 | q.s. to 100 |
| PROPYLENE GLYCOL | 7 | 7 |
| HYDROXYETHYLCELLULOSE | 2 | 2 |
| CARBOMER | 1 | 1 |
| ACRYLATES/METHACRYLAMIDE COPOLYMER | 0.3 | 0.3 |
| SODIUM HYDROXIDE | 1 | 1 |
| PARFUM (FRAGRANCE) | 0.6 | 0.6 |
| SODIUM SULPHITE | 0.5 | 0.5 |
| ERYTHORBIC ACID | 0.3 | 0.3 |
| EDTA | 0.2 | 0.2 |
| TOLUENE-2,5-DIAMINE SULPHATE | 1.271 | 0.4 |
| p-AMINOPHENOL | 0.19 | 0.5 |
| HYDROXYETHYL 3,4-METHYLENE-DIOXYANILINE HCL | — | 1 |
| 2-AMINO-3-HYDROXYPYRIDINE | 0.07 | 0.13 |
| m-AMINOPHENOL | 0.065 | 0.1 |
| 2,4-DIAMINOPHENOXYETHANOL HCl | 0.009 | — |
| 4-CHLORORESORCINOL | 0.547 | — |
| 2-METHYLRESORCINOL | 0.306 | — |
| ETHANOLAMINE (MEA) | 3.7 | 3.7 |
| Total dyes | 2.458 | 2.13 |

It should be noted that formula F8* according to the invention contains 13% less dyes, and in particular 68% less p-toluenediamine (PTD).

Test 1: Colour Result

The colour test was conducted on 100% white homogenised natural IHIP locks.

Formulas F1 to F8, suitably mixed with activators A1 to A4, were applied to the locks.

In particular:

Compositions F1 and F2* were mixed at the ratio of 1:1.5 with activator A3 from Table 1.

Compositions F3 and F4* were mixed at the ratio of 1:1.5 with activator A2 from Table 1.

Compositions F5 and F6* were mixed at the ratio of 1:1.5 with activator A4 from Table 1.

Compositions F7 and F8* were mixed at the ratio of 1:1.5 with activator A3 from Table 1.

The colour was left to develop on the locks for 35 minutes at a temperature of 30° C.

The locks were then rinsed and dried.

The colour result, in terms of level and tone, was evaluated by 6 industry experts, who scored it on the following scale:

1 colour result similar to reference STANDARD 2 slight difference in level and/or tone compared with reference STANDARD 3 colour result different from reference STANDARD.

The mean value of the scores is shown in Table 4.

TABLE 4

Lock colour test.

| Formulas evaluated | MEAN COLOUR RESULT SCORE |
|---|---|
| F1 vs. F2* | 1.16 |
| F3 vs. F4* | 1.3 |

TABLE 4-continued

| Lock colour test. | |
|---|---|
| Formulas evaluated | MEAN COLOUR RESULT SCORE |
| F5 vs. F6* | 1 |
| F7 vs. F8* | 1.5 |

The colour result in all shades is also similar without resorcinols or derivatives thereof.

Test 2: Stability of Emulsion.

Compositions F1 to F6 were placed in glass jars for 15 days at 50° C. (accelerated stability protocol), then removed and kept at room temperature for 24 h. They were then visually examined by 6 experts to evaluate whether the emulsion had separated or was homogeneous and consequently stable.

TABLE 5

| Composition stability test. | |
|---|---|
| COMPOSITION | EVALUATION |
| F1 | NOT SEPARATED |
| F2* | NOT SEPARATED |
| F3 | SLIGHT SEPARATION |
| F4* | NOT SEPARATED |
| F5 | SLIGHT SEPARATION |
| F6* | NOT SEPARATED |

The compositions according to the invention are more stable over time due to the smaller amount of sulphate dyes they contain.

Test 3 Colour Fade: Resistance of Colour to Washing

A Konica Minolta colorimeter was used to evaluate colour fading.

In the CIELAB colour space, L* indicates sheen and a* and b* are the colour coordinates. a* and b* indicate the colour directions: +a* is the direction of red, −a* is the direction of green, +b* is the direction of yellow and −b* is the direction of blue.

Differences in colour can be expressed by the ΔE values, which are defined by the following equation:

$$\Delta E=[(\Delta L^*)2+(\Delta a^*)2+(\Delta b^*)2]^{1/2}$$

For the following examples, parameter ΔE was considered.

The lower the value of ΔE, the less the colour will fade after washing.

The test was conducted on IHIP hair locks level 10 Lightest Blonde, which were dyed with formulations F1 F2*F3 and F4* mixed with activator A3 at the ratio of 1:1.5.

The product was left on the hair for 30 minutes at the temperature of 30° C.

The locks were then rinsed, dried and measured with the colorimeter.

The locks were then washed 9 times consecutively with Alfaparf Salon Line shampoo, dried and measured again with the colorimeter.

TABLE 6

| Colour fade due to washing | |
|---|---|
| Formula | ΔE |
| F1 | −6% |
| F2* | −4% |
| F3 | −9% |
| F4* | −7% |

Table 6 shows the % fade values after 9 washes, and the result obtained is comparable.

The invention claimed is:

1. Hair colouring compositions free of resorcinol, 2-methyl resorcinol, 4-chloro resorcinol and resorcinol derivatives, and free of methoxymethyl-p-phenylenediamine, comprising at least one primary dye selected from p-toluenediamine sulphate, p-aminophenol, N-methyl-p-aminophenol sulphate and 1-hydroxyethyl-4,5-diamino pyrazole sulphate, and at least two secondary dyes selected from hydroxyethyl 3,4-methylenedioxyaniline HCl, 2-amino-3-hydroxypyridine and 2-methyl-5-hydroxyethyl-aminophenol, or at least two primary dyes selected from p-toluenediamine sulphate, p-aminophenol, N-methyl-p-aminophenol sulphate and 1-hydroxyethyl-4,5-diamino pyrazole sulphate, and at least one secondary dye selected from hydroxyethyl 3,4-methylenedioxyaniline HCl, 2-amino-3-hydroxypyridine and 2-methyl-5-hydroxyethyl-aminophenol.

2. Compositions according to claim 1 comprising additional oxidative dyes.

3. Compositions according claim 2 containing at most 6% by weight of total oxidative dyes and at most 3% by weight of p-toluene diamine.

4. Compositions according to claim 3 containing at most 2% by weight of p-toluenediamine.

5. Compositions according to claim 1 further comprising one or more additives, solvents, surfactants, emulsifiers, humectants, thickeners or conditioners.

6. Compositions according to claim 1 comprising an alkalising agent selected from ammonia, monoethanolamine, 1-amino-2-propanol, 2-amino-2-methyl-propanol, 2-amino-2-methyl-1,3 propanediol, 2-amino-2-ethyl-1, 3-propanediol, tris(hydroxymethyl)-aminomethane), sodium hydroxide, potassium hydroxide, urea, allantoin, arginine, lysine, tripotassium phosphate, sodium saccharin, triethanolamine or combinations thereof.

7. Compositions according to claim 1 in "ready to use" form comprising two or more ingredients to be mixed before use.

* * * * *